US005557352A

United States Patent [19]

Nordquist

[11] Patent Number: 5,557,352
[45] Date of Patent: Sep. 17, 1996

[54] METHOD AND APPARATUS FOR MEASURING THE VISUAL ACUITY OF THE HUMAN EYE DURING AND IMMEDIATELY AFTER OCULAR SURGERY

[75] Inventor: Robert E. Nordquist, Oklahoma City, Okla.

[73] Assignee: Wound Healing of Oklahoma, Oklahoma City, Okla.

[21] Appl. No.: 371,957

[22] Filed: Jan. 12, 1995

[51] Int. Cl.$^6$ ............................. A61B 3/02; A61B 3/00
[52] U.S. Cl. .................. 351/237; 351/244; 351/246
[58] Field of Search ........................... 351/222, 237, 351/239, 243, 244, 245, 246, 211, 223

[56] References Cited

U.S. PATENT DOCUMENTS

| | | | |
|---|---|---|---|
| 268,016 | 11/1882 | Hardy | 351/222 |
| 484,055 | 10/1892 | Sherman | 351/222 |
| 1,510,114 | 9/1924 | Thorner | 351/211 |
| 1,747,844 | 2/1930 | Ritholz | 351/222 |
| 2,523,007 | 9/1950 | Glazer | 351/223 |
| 3,664,631 | 5/1972 | Guyton | 351/211 |
| 3,905,688 | 9/1975 | Decker et al. | 351/222 |
| 4,679,921 | 7/1987 | Yamada | 351/222 |
| 5,455,645 | 10/1995 | Berger et al. | 351/223 |

OTHER PUBLICATIONS

Edmund Scientific, *Off-the-Shelf Optics & Components for OEM and Research Applications*, #14N7.
Seller Instrument, *Dioptometer*, PN 7680631.

*Primary Examiner*—Huy Mai
*Attorney, Agent, or Firm*—Head, Johnson & Kachigian

[57] ABSTRACT

A method and apparatus are provided for measuring the visual acuity and refraction of the human eye during and immediately after ocular surgery. The method includes supporting a measuring means anterior to, and in line with the visual axis of, the eye and measuring the visual acuity of the eye using patient responses to visual prompts. The apparatus includes an elongate housing having an ocular aperture. A collimating lens is positioned within the housing adjacent to the ocular aperture and a resolution target is located above the collimating lens. A light source is used to illuminate the resolution target. The distance from the collimating lens to the target is adjustable, and refractive shift is indicated.

9 Claims, 5 Drawing Sheets

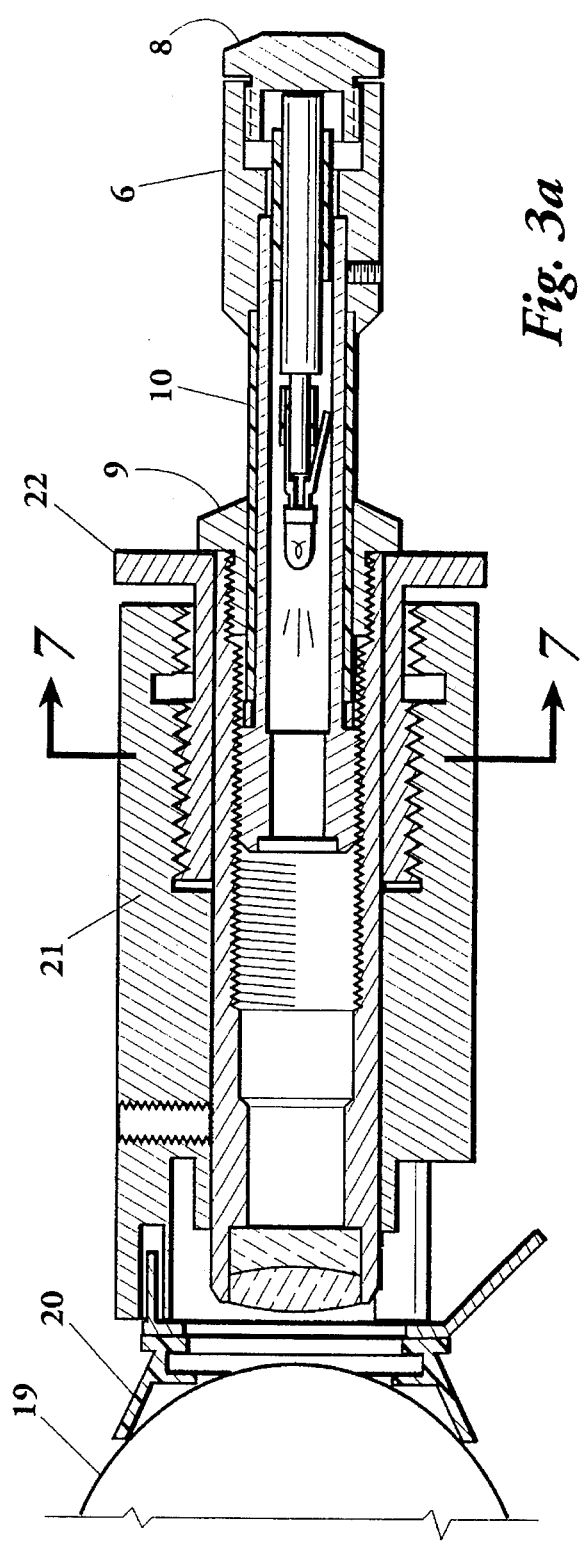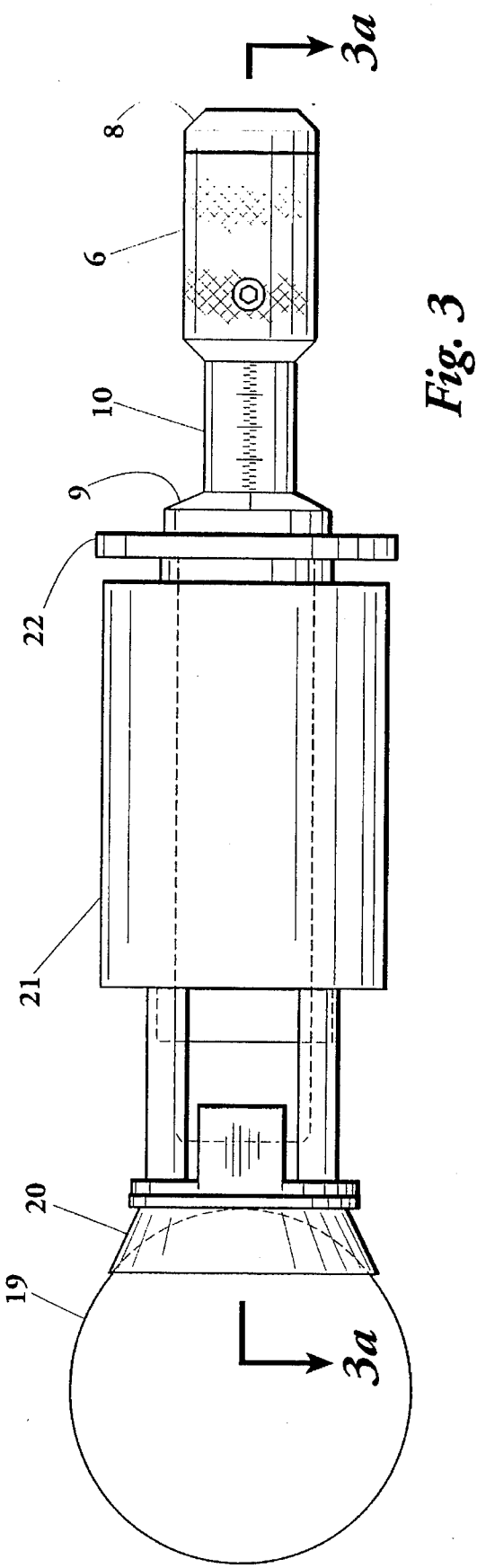

METHOD AND APPARATUS FOR MEASURING THE VISUAL ACUITY OF THE HUMAN EYE DURING AND IMMEDIATELY AFTER OCULAR SURGERY

BACKGROUND OF THE INVENTION

This invention relates generally to ocular surgical procedures and instruments, and, more specifically, to a method and apparatus for measuring the visual acuity of the human eye, utilizing patient responses to visual prompts, during and immediately after ocular surgery. The invention is particularly useful in the field of corneal refractive surgery.

The cornea is the transparent tissue constituting the anterior sixth of the outer wall of the eye; its normal radius of curvature being 7.8 mm. Deviations from the normal shape of the corneal surface can produce errors of refraction in the visual process if the remainder of the eye's dimensions do not scale accordingly. The emmetropic eye, in a state of rest, focuses the image of distant objects exactly on the retina. Such an eye enjoys distinct vision for distant objects without effort. Any variation from this standard constitutes ametropia, a condition in which the eye at rest is unable to focus the image of a distant object on the retina.

Hyperopia, or far-sightedness, is an error of refraction in which, with the eye at rest, parallel rays from distant objects are brought to focus behind the retina. This can be caused by a relatively flat corneal surface and a concomitant decrease in the angle of refraction of rays as they pass through the refractive media of the cornea, causing a convergence or focus of the rays at a point behind the retina.

Myopia, or near-sightedness, is that refractive condition in which parallel rays are brought to focus in front of the retina. One condition that commonly causes myopia is an excessively steep corneal curvature. Thus, the angular refraction of rays is greater as they pass through the refractive media of the cornea, and the over-refracted rays converge or focus in front of the retina in the vitreous of the eye. When the rays reach the retina they become divergent, causing a blurred image.

Astigmatism is a condition in which the front surface of the cornea is not truly spherical. Although the eye may be perfectly healthy, the corneal surface may be toroidal in nature as a result of orthalyonal meridians having discrepancies in curvature. This causes the horizontal and vertical meridians to focus apart from one another. Some degree of astigmatism is normal; however, more severe astigmatism causes the blurring of lines aligned at a particular angle. A person with astigmatism may see horizontal lines clearly, but vertical lines blurred, or the blurring may occur in an oblique meridian.

The normal treatment of refractive error involves the use of eyeglasses or contact lenses, both of which have well-known disadvantages. Consequently, recent research has been directed to surgical procedures to change the refractive condition of the eye. Such procedures are generally referred to as "kerato-refractive techniques," particular examples of which are radial keratotomy, keratomileusis, keratomileusis-in-situ, epikeratophakia, keratophakia, photo-refractive keratectomy, and mechanical keratectomy.

In radial keratotomy the cornea is reshaped to correct myopia through the use of a plurality of incisions made to extend radially out from the central axis of the eye. The associated scarring essentially stress-relieves the cornea, causing the cornea to become flatter and less powerful in the central regions due to the outward force on the periphery by the eye's intraocular pressure.

Keratomileusis involves the regrinding of a corneal lamella into a meniscus to correct myopia or hyperopia. In this procedure, a portion of the cornea is excised (keratectomy) in the shape of a disk. The corneal disk is then frozen and its shape is altered by the use of a lathe. After lathing, the disk is thawed and sutured onto the keratectomy bed. In keratomileusis-in-situ the underlying stroma is re-shaped to correct the refractive error present in the eye.

Keratophakia involves removing corneal tissue and sandwiching another material therebetween. Typically, a homograft is ground into a convex lens which is placed interlamellarly to correct aphakic hypermetropia. In epikeratophakia a corneal tissue applique is attached to the corneal surface to correct the refractive error such that the patient, in effect, receives a "living" contact lens.

Photo-refractive keratectomy, also known as photoablation, and corneal contouring are techniques that correct refractive error by modifying the contour of the cornea through tissue removal. In photoablation a laser is used to reshape the surface of the cornea by removing intra-stromal tissue. Corneal contouring, on the other hand, is a mechanical keratectomy procedure that re-profiles the cornea by rotating and oscillating a knife edge about the optical axis of the cornea, scraping the cornea until the refractive error has been substantially corrected.

A number of these techniques, derivatives and improvements thereof, and instruments used in connection therewith are described in further detail in various medical resource publications and issued patents. For example, U.S. Pat. Nos. 4,526,171; 4,619,259; 4,688,570; 4,691,715; 4,691,716; and 4,665,914 relate to radial keratotomy, while U.S. Pat. Nos. 4,662,370; 4,432,728; 2,249,906; 2,480,737, 4,750,491; and 4,763,651 pertain to corneal trephines. Laser or electrical surgical procedures and instruments are disclosed in U.S. Pat. Nos. 4,665,913; 4,718,418; 4,729,372; 4,770,172; 4,798,204; 4,732,148; 4,724,522; 4,838,266; 4,840,175; 4,381,007; 4,326,529; 4,994,058; 4,988,348; 4,973,330; and 4,941,093. U.S. Pat. Nos. 4,947,871; 4,997,437; 4,173,980; and 4,834,748 concern techniques and devices for grinding or abrading the corneal surface, and mechanical keratectomy using a scraping mechanism is revealed in U.S. Pat. No. 5,063,942. Other methods of surgical manipulation of the cornea are disclosed in U.S. Pat. Nos. 4,907,585; 4,907,587; 4,766,895; 4,452,235; 4,671,276; 4,976,719; 4,712,543; and 4,461,294.

An excellent resource on corneal surgery in general is *Microsurgery of the Cornea*. J. Barraquer and J. Rutllan (1984) Ediciones Scriba, S. A.—Barcelona.

Although the above-identified surgical procedures have a broad application in the correction of hyperopic, myopic, and astigmatic errors, there are significant obstacles yet to be overcome. For instance, keratophakia, keratomileusis and epikeratophakia are expensive, complicated procedures, limited in success by scarring in the corneal stromal interfaces. And eyes having undergone keratotomy may similarly suffer from post-operative instability, a significant decrease in impact resistance, scarring, glare, and vision fluctuation. Precise corneal reshaping is further hindered due to individual variances in wound healing, the resiliency of the cornea, the effect of fluid pressure, and the skill of the surgeon in applying the reshaping tool.

All of this leads to perhaps the most significant problem associated with kerato-refractive surgery—unpredictability of result. In fact, the incidence of over-or under-correction associated with these surgeries serves to dissuade many suitable candidates from undergoing a surgical refractive correction. In addition, errors in correction of refractive shift (hereinafter sometimes referred to as "corrective error"), especially radial keratotomy hyper-corrections, many times necessitates a second surgical procedure to rectify the over or under correction. The problem is no different for laser surgeries. Intra-stromal ablation using infrared wavelengths has not yet reportedly yielded the precision necessary to achieve predictable postoperative results, and surface ablation with an excimer laser is reported to result in unpredictability attributable to high degrees of variability of ablation depths per laser pulse. Thus, it is not possible to precisely pre-calculate a procedure to achieve a defined post-operative result.

Owing to the difficulties in calculating a proper surgical protocol and predicting kerato-refractive surgical results to ensure accurate and precise correction, there is a need for a method and apparatus to perform visual acuity testing, utilizing real-time patient responses to visual prompts, during and immediately after ocular surgery.

Presently, the patient's corneal topography, refraction and visual acuity are determined prior to the initiation of the procedure. Based upon this pre-operative testing, the surgical protocol for the corrective procedure is calculated using given parameters. While the patient's changed corneal topography may be evaluated during the operation, only long after the completion of the procedure, is the patient's "corrected" visual acuity subject to evaluation.

As it stands now, meaningful evaluation of a patient's corrected visual acuity is delayed to between two and four weeks after the time of surgery, and even longer in the case of radial keratotomy. The lack of a method and device to determine a patient's visual acuity during and immediately after the corrective procedure deprives the surgeon of the ability to accurately adjust the surgical protocol during the procedure to take into account differences in surgical performance or individual patient variables such as corneal density and the degree of corneal hydration, variables which may be concealed in the pre-operative stage. The availability of a method and apparatus to measure the patient's visual acuity during and immediately after an ocular surgical procedure would therefore increase surgical precision and accuracy of result by allowing the surgeon to make on-the-spot adjustments to standard surgical protocol in response to patient cues. This should decrease both the instance of over and under correction associated with kerato-refractive surgery and the resultant necessity for second surgeries.

Though the above discussion has focused on refractive errors and keratorefractive surgical corrections, it should be understood that the method and apparatus disclosed and claimed herein have utility under any conditions in which patient responses to visual prompts during or immediately after ocular surgery are desirable.

SUMMARY OF THE INVENTION

It is therefore an object of the present invention to provide a new and useful method and apparatus for measuring the visual acuity of the human eye, utilizing patient responses to visual prompts, during and immediately after ocular surgery.

It is a further object of the present invention to provide a method and apparatus for measuring the visual acuity of the human eye during and immediately after surgery to correct refractive errors of hyperopia, myopia, and astigmatism, whereby a minimum disturbance is imposed on the eye system and the chance of corrective error is reduced.

It is another object of this invention to provide a method and apparatus to surgeons that allows for surgical precision and corrective accuracy in cases of keratorefractive surgery, which method is easily performed by the ophthalmic community and which apparatus is readily adaptable to commonly used ocular surgical instruments and protocols.

With these and other objects in view, the present invention contemplates a method for measuring the visual acuity of the human eye during and post corneal corrective procedures which comprises supporting a measuring means anterior to, and in line with the visual axis of, the eye and measuring the visual acuity of the eye using patient responses to visual prompts emanating from the measuring means. In one embodiment a ring is fixed about the cornea of the patient's eye so as to be coaxial with the visual axis of the eye. If the epithelium of the patient's eye has been removed through keratectomy, a transparent and powerless conformal contact lens is placed on the eye so as to provide an optically transmissive surface while not influencing the absolute refraction of the eye during measurement. A support housing is then attached to the ring. Introduced inside the support housing is a means for measuring the patient's visual acuity. The patient responds to questions regarding the clarity of visual prompts emanating from the measuring means, and, based upon such responses, the visual acuity of the patient is determined.

Another object of the invention is to provide a mechanical apparatus capable of easily being used by a surgeon for measuring the visual acuity of a patient during and after a corneal corrective procedure which minimally disturbs the eye system but accurately determines the patient's visual acuity.

The apparatus used to achieve the objects of this invention includes an elongated, tubular housing having an ocular aperture. A collimating lens is positioned within the housing adjacent to the ocular aperture and a resolution target is located above the collimating lens. Means are provided for illuminating the resolution target and for adjusting the degree of separation between the collimating lens and the resolution target.

In one embodiment of the apparatus, the housing includes a flange at the end opposite the ocular aperture. The housing is insertable into a micrometer casing or other ocular platform such that the flange supports the housing within the casing or platform in a position whereby the ocular aperture is fixed approximately 6 mm from the patient's eye. A tubular target piston threadably connects to the interior of the housing above the collimating lens, the piston supporting the resolution target above the lens and having a neck that extends through the flange and connects to a knob, such that turning the knob adjusts the degree of separation between the lens and the target. A manually actuated, battery-powered light source is self-contained within the apparatus, the light source being housed within the tubular target piston above the resolution target. A battery for the light source is located within the knob, and the light source is actuated by the manual rotation of a cap threadably connected to the knob.

An important technical advantage of the current invention is that measurement of a patient's visual acuity and refraction is made possible during and immediately after keratorefractive surgery utilizing a method and apparatus which allow for such a determination based upon the patient's responses to visual prompts. The invention allows for the measurement of absolute refractive error and the refractive shift of the patient's eye after a corneal corrective procedure and provides a method and apparatus to determine the patient's pre-and post-operative uncorrected visual acuity and pre-and post-operative best corrected visual acuity. Uncorrected visual acuity will be obtained when the target is set at the zero or infinity position. Best corrected visual acuity without regard to astigmatism will be obtained when the target is set at the position representing the patient's spherical equivalent refraction.

The device can also be used as a tool to determine the visual acuity and field of vision of patients with glaucoma. Presently, these patients are given a paper target to hold up in front of their eye, but many fail to use it correctly.

A better understanding of the invention will be obtained from the ensuing description taken in conjunction with the accompanying drawings and claims.

BRIEF DESCRIPTION OF THE DRAWINGS

FIG. 3 is a side elevational view of the preferred embodiment of the apparatus as supported for use by a conventional ocular surgical platform.

FIG. 3a is a cross-sectional view of the preferred embodiment of the apparatus as supported for use by a conventional ocular surgical platform taken along the line B—B of FIG. 3.

FIG. 7 is a cross-sectional view of the apparatus taken along the line C—C of FIG. 3a.

DETAILED DESCRIPTION OF THE PREFERRED EMBODIMENT

Figure 1:
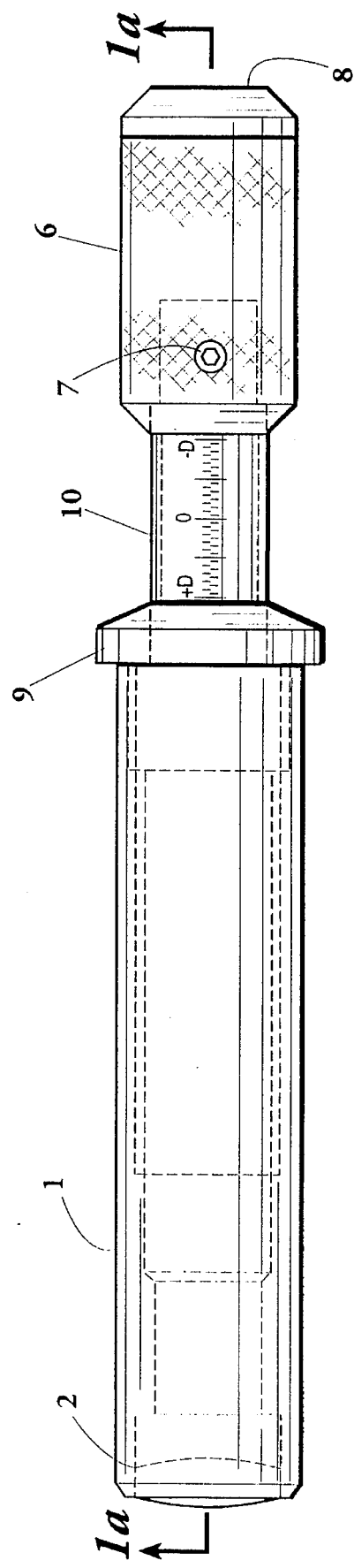
FIG. 1 is a side elevational view of the preferred embodiment of the apparatus of this invention.

Before explaining the present invention in detail, it is to be understood that the invention is not limited in its application to the details of the construction and arrangement of parts illustrated in the accompanying drawings. The invention is capable of other embodiments and of being practiced or carried out in a variety of ways. It is to be understood that the phraseology and terminology employed herein is for the purpose of description and not of limitation.

A collimator is an optical instrument which consists of a well corrected objective lens with an illuminated target or retical at its focal plane. The collimator can generate three manners of light rays which, in turn, create the imagery observed by the viewer. For an emmetropic eye, the target is at the focal plane which results in parallel rays exiting the collimator. The imagery is perceived as emanating from infinity. For a myopic eye, whereby distant rays focus in front of the retina, the target is moved forward. This creates divergent rays from the collimator. The unaided myopic eye when observing divergent rays focuses the imagery once again at the retina. For the hyperopic eye, the target is backed out, causing convergent rays to encounter the cornea. The focus moves forward, thus also imaging at the retina.

The method includes supporting a measuring means anterior to, and in line with the visual access of, the eye and measuring the visual acuity of the eye using patient responses to visual prompts emanating from the measuring means. Using this method, the visual acuity of the patient can be measured before, during or after a corneal corrective procedure. In the event that the eye's epithelium has been removed, such as for marking or after ablation, a conformal-style contact lens must be applied to the eye in order to provide an optically transmissive surface. An appropriate contact lens is approximately 8 mm in diameter and 35 µm thick. The lens is plano or powerless so as not to influence the absolute refraction of the eye. The contact lens can either be applied by hand with a loosely coupled sponge-like hollow shaft handle or in any other manner consistent with the utilization of the below described apparatus.

The measuring means is positioned approximately 6 mm from the eye. The measuring means may be supported anterior to the eye at the appropriate distance from the eye by conventional ocular surgical equipment. Fixation rings which are positionable about the cornea of the eye so as to be coaxial with the visual access of the eye are well known in the art. A support housing, such as a micrometer casing, is positioned upon the fixation ring, the support housing being coaxially supported upon the fixation ring. A means for measuring the visual acuity of the eye is then positioned within the support housing and the visual acuity of the eye is measured using the patient's responses to visual prompts emanating from the measuring means. The measuring means contains a visual target for the patient. The measuring means is adjusted until the patient feels the target is at its best focus. A calibrated measurement is made and converted into the residual refractive error possessed by the patient. The resolution obtained from observing the target will likewise be convened into units of visual acuity. If the patient's uncorrected visual acuity is desired, the measuring means will be set to a setting representing infinity. A measurement can then be taken of the patient's visual acuity. At the conclusion of this test, the contact lens is removed.

Figure 1A:
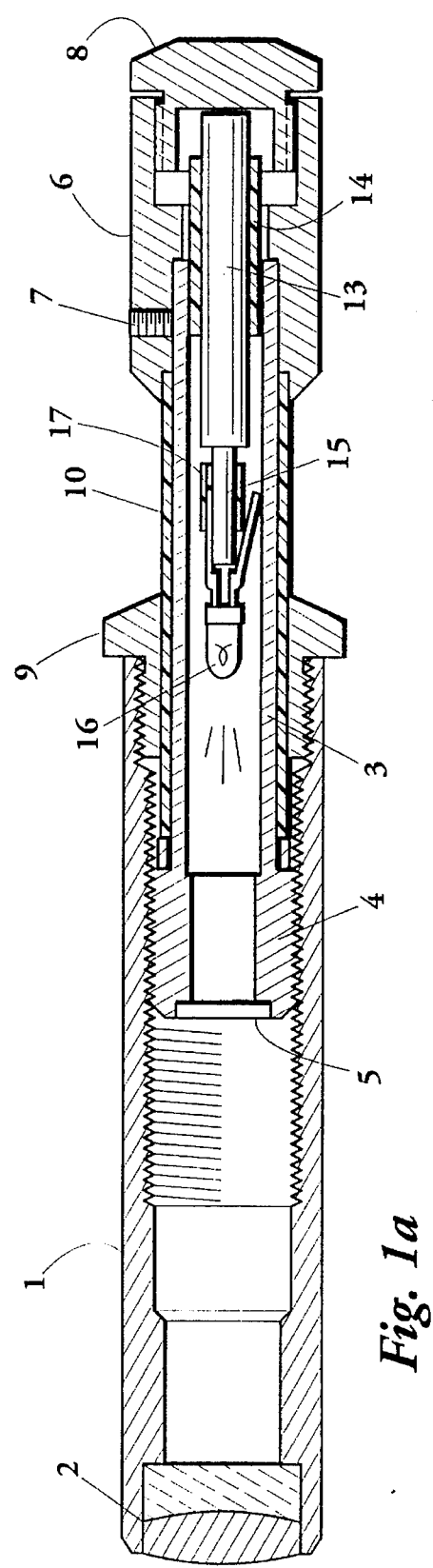
FIG. 1a is a cross-sectional view of the apparatus of FIG. 1 taken along line A—A of FIG. 1.
Figure 2:
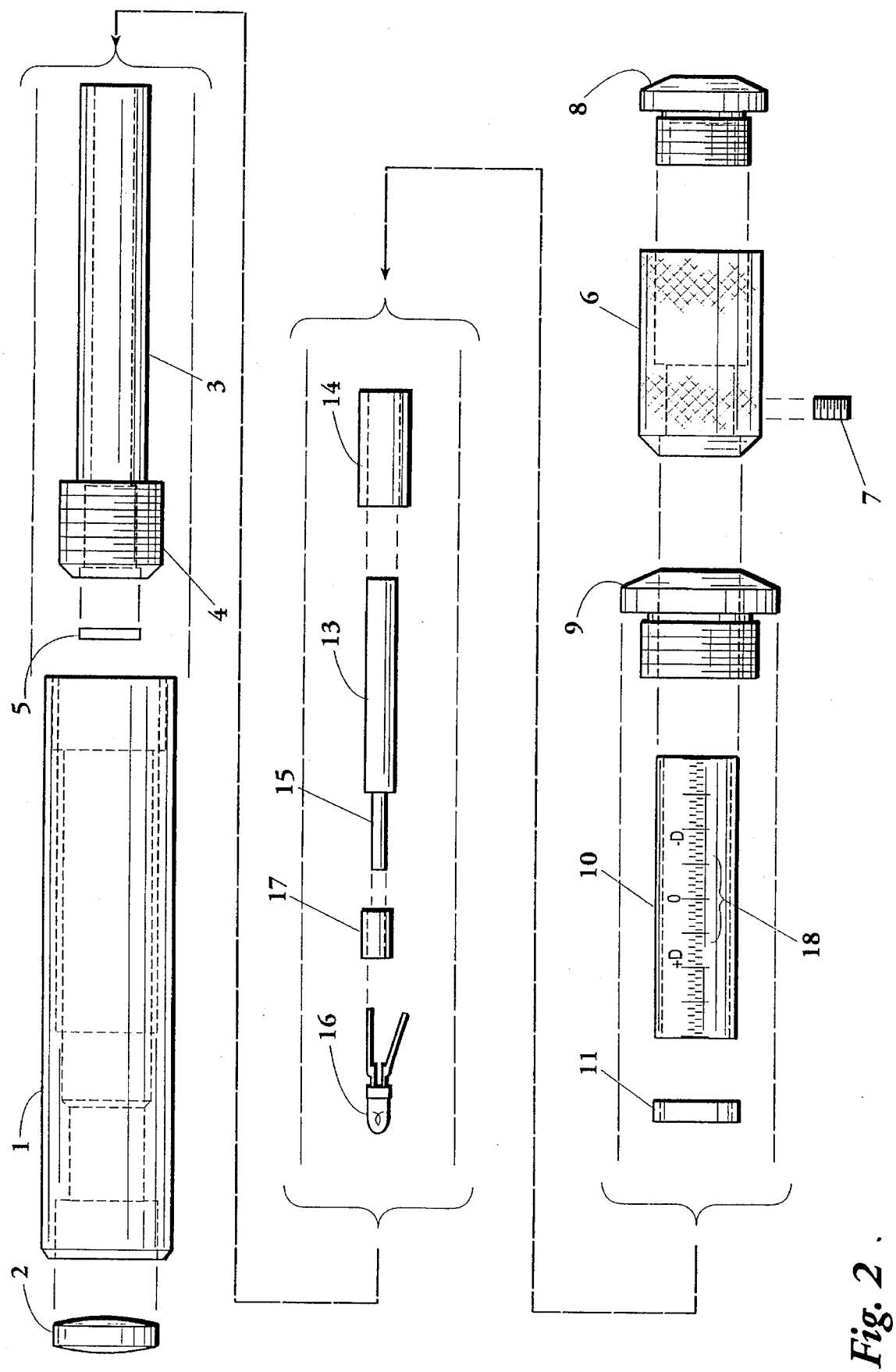
FIG. 2 is an exploded view of the preferred embodiment of the apparatus.

Referring now to FIGS. 1, 1a, and 2 and the apparatus of the invention, a collimator housing is indicated by the reference numeral 1. Collimator housing 1 is tubular and contains an ocular aperture at which is placed a collimating lens 2. The collimating lens 2 used in the preferred embodiment of the invention is commonly referred to as a doublet. Collimating lens 2 is a two element lens, i.e. two lens bonded together, which in union form the objective lens for the system. Collimating lens 2 is also achromatic. In other words, it is corrected for color.

A target piston 3 is provided for threadable insertion into collimator housing 1. At its end that bears closest to the ocular aperture of collimator housing 1, target piston 3 is provided with a threaded target piston head 4, which is slightly larger in diameter than the shaft of target piston 3. Target piston head 4 supports target 5. Target 5 is translucent except for its eye chart characters. The end of target piston 3 opposite target piston head 4 is connected by set screw 7 to knob 6. By turning knob 6 the position of target piston 3, and the concomitant position of target 5, from collimating lens 2 may be adjusted, owing to the action of threaded target piston head 4.

Other means may be provided for adjusting the degree of separation between collimating lens 2 and target 5 besides the threaded piston assembly heretofore described. A pressed-fit friction mechanism would also perform the function of adjusting the degree of separation. In such an embodiment, target piston 5 would be slidably adjustable within collimator housing 1 such that target 5 could be pressed toward collimating lens 2 or pulled away therefrom without the necessity of turning threaded members.

Plastic spacer 11 slides over target piston 3 and abuts target piston head 4. Plastic spacer 11 limits the degree to which target piston 3 may be backed away from collimator lens 2. When threaded target piston head 4 is at its position farthest from collimator lens 2, plastic spacer 11 will abut flange insert 9.

Like plastic spacer 11, sleeve 10 slides over target piston 3. Like target piston 3, sleeve 10 is connectable to knob 6. Sleeve 10 contains thereon indicia corresponding to a calculated refractive shift. The indicia on sleeve 10 is preferably indicated in plus or minus diopters. A plus diopter reading corresponds to a hyperopic condition, while a minus diopter reading corresponds to a myopic condition. Threaded flange insert 9 contains an aperture through which sleeve 10 extends to knob 6, threaded flange insert 9 being threadably connectable to the end of collimator housing 1 opposite of collimating lens 2.

A light source is contained within tubular target piston 3 above target 5. In the preferred embodiment of the invention, as illustrated in FIGS. 1, 1a, 2 and 3a, the light source comprises a battery 13 having a terminal 15 to which is connected a bulb 16 having two conductive leads extending therefrom. One lead of bulb 16 is connected to battery terminal 15 by a cylindrical plastic lead insulator 17. The other lead from bulb 16 is angled to contact the inside wall of target piston 3. Around the circumference of battery 13 is plastic battery insulator 14, which insulates battery 13 from the inside walls of target piston 3 and knob 6. The light source assembly just described is actuated when cap 8 is fully threaded into knob 6, such that the inner surface of cap 8 contacts battery 13. This completes a circuit, and light is obtained from bulb 16.

Figure 4:
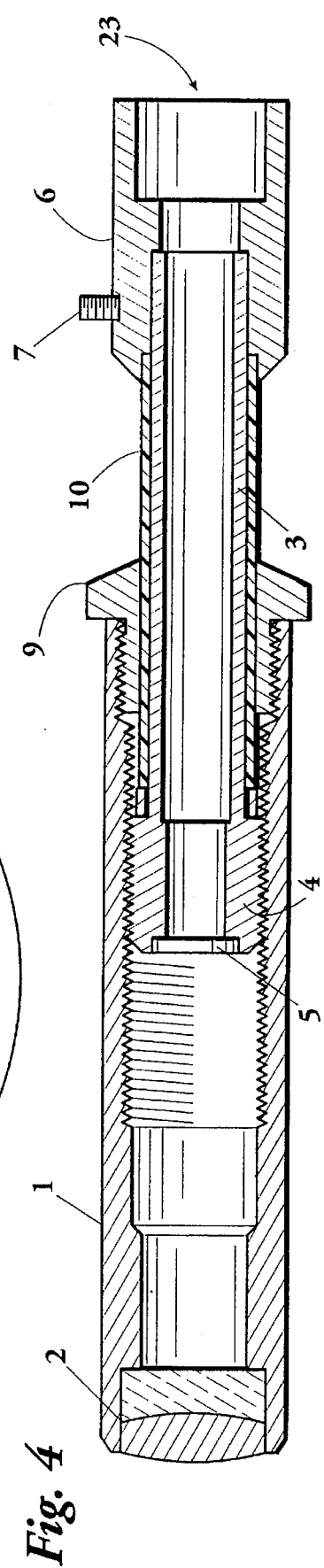
FIG. 4 is a cross-sectional view of an alternate embodiment of the apparatus of this invention.

Other means may be utilized to provide light above target 5, such as room light or fiber optic illumination through the top of the apparatus. An embodiment of the invention wherein these alternative light sources may be used is shown in FIG. 4. In FIG. 4 it can be seen that cap 8 has been removed, along with the light source assembly comprising the bulb and battery mechanism. A light source channel 23 is thereby created. Using this embodiment, target 5 may be illuminated with room light or any other such light emitting devices that may be directed towards light source channel 23. Specifically, a fiber-optic illuminator may be inserted into light source channel 23 to provide target illumination.

Turning now to FIGS. 3 and 3a, the apparatus of the invention is shown as supported in a conventional ocular surgical platform. To human eye 19 is attached fixation ring 20. Fixation ring 20 may be one of several well known fixation rings which are positionable about the cornea of an eye so as to be coaxial with the visual access of the eye. Attached to fixation ring 20 is a support housing 21, such as an ablation micrometer, with means at the bottom of housing 21 to coaxially support the housing upon fixation ring 20. A micrometer nut 22 is part and parcel to support housing 21 and is not a part of the present invention. However, in this case micrometer nut 22 functions to provide a support ledge upon which rests flange insert 9. The length of collimator housing 1 should be such that collimating lens 2 is supported approximately 6 mm from human eye 19 when flange insert 9 is flush against micrometer nut 21.

The optical characteristics of the preferred embodiment of the collimator of the present invention are as follows:

TABLE 1

VA COLLIMATOR OPTICAL CHARACTERISTICS OF THE PREFERRED EMBODIMENT

| | |
|---|---|
| Effective Focal Length | 25.24 mm |
| Working Distance From Cornea | 6 mm |
| Collimator Exit Pupil Diameter | 6 mm |
| Typical Pupil of the Eye | 4 mm |
| f/# (Collimator alone) | 4.2 |
| f/# (with eye) | 6.3 |
| Projected Field of View | ±5° |
| Target Diameter | 4.4 mm |

Referring now to Table 1, the effective focal length means the focal length of collimator lens 2. The collimator exit pupil diameter is defined as the diameter of the above-described ocular aperture. The f/# as specified is calculated by dividing the focal length by the aperture diameter. The projected field of view refers to the number of degrees of inclination required above the focal plane to view the top of resolution target 5 and the number of degrees in the opposite direction required to view the bottom of target 5.

The system characteristics of the apparatus of the invention are as follows:

TABLE 2

VA COLLIMATOR SYSTEM CHARACTERISTICS OF THE PREFERRED EMBODIMENT

| | |
|---|---|
| 20/20 Vision | 1 Arc Minute Line Width |
| 1 Arc Minute at Target | 7 µm Line Width |
| 20/20 Target Line Frequency | 68 Line Pairs/mm |
| MTF at 20/20 Resolution (axial) | 70% |
| MTF at 20/20 Resolution (2.5°) | 49% |
| 20/20 Depth of Focus (10% MTF) | ±.17 mm |
| ¼ Diopter Target Shift | .16 mm |

Referring to Table 2, MTF means Modulation Transfer Function.

Table 3 below shows the target shift as a function of refractive correction. These numbers correspond to the markings of indicia on sleeve 10.

TABLE 3

TARGET SHIFT AS A FUNCTION OF REFRACTIVE CORRECTION

| Patient Correction (In Diopter) | Target Shift (In mm) |
|---|---|
| +5 | +3.62 |
| +4 | +2.82 |
| +3 | +2.06 |
| +2 | +1.34 |
| +1 | +.65 |
| 0 | 0 |
| −1 | −.62 |
| −2 | −1.21 |
| −3 | −1.78 |
| −4 | −2.32 |
| −5 | −2.84 |

Figure 5:
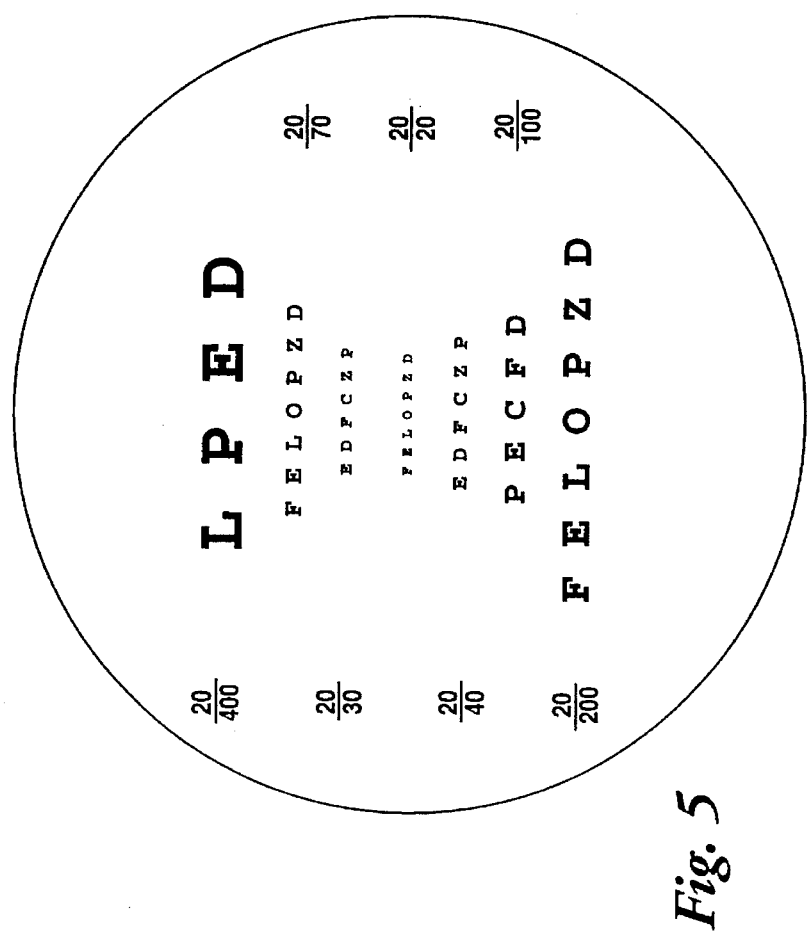
FIGS. 5 and 6 are examples of target facings for use in connection with the apparatus of this invention.
Figure 6:
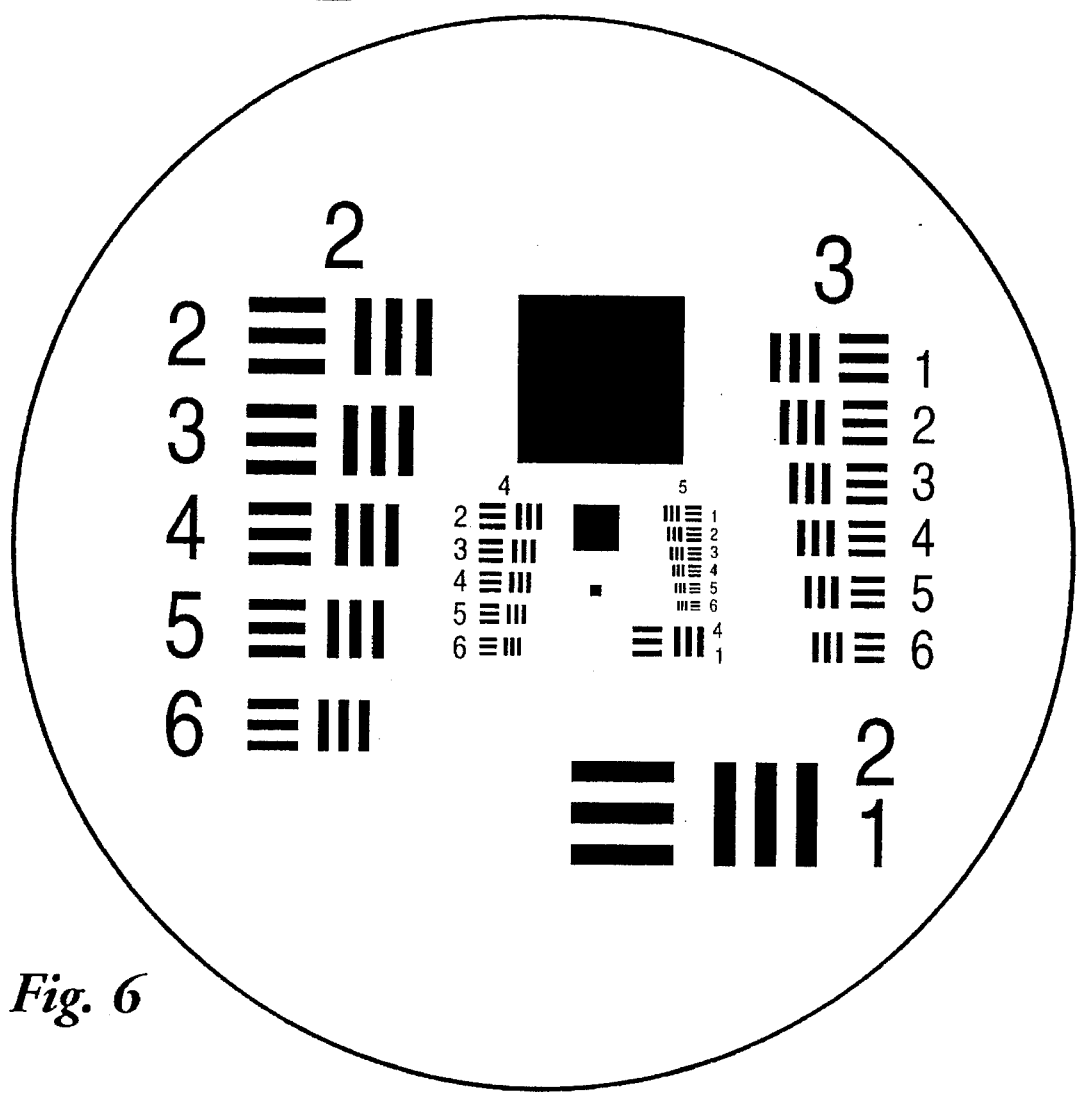

FIGS. 5 and 6 show two possible types of resolution targets to be used in connection with the apparatus of the present invention. FIG. 5 is a novel target in which the size of the target characters are increased from the center towards the periphery of the target area. FIG. 6 represents a target modeled upon the well known 1951 Air Force Resolution Target. Again, the target characters increase in size from the center point of the target to its periphery.

Figure 7:
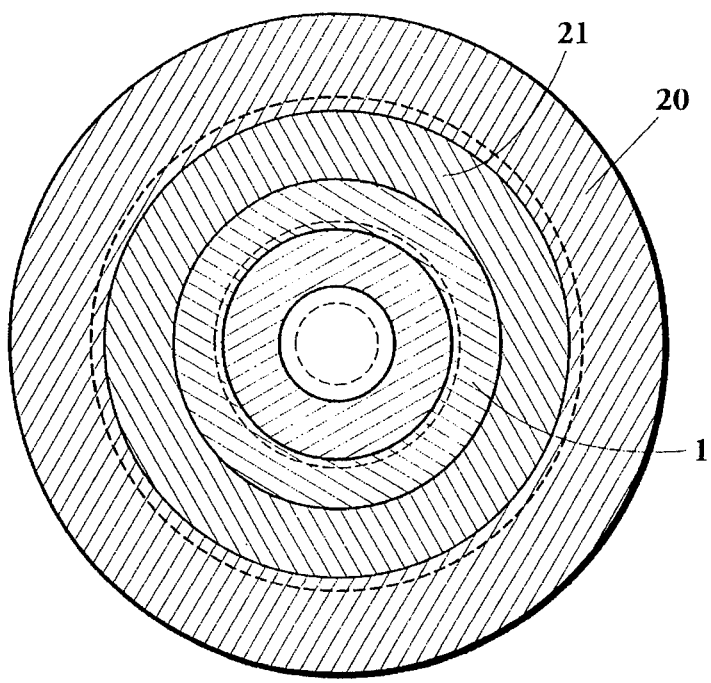

FIG. 7 shows a cross-sectional view of the apparatus taken along the line C—C of FIG. 3a. This can be considered a patient's perspective view. It can be seen that fixation ring 20 circumscribes ablation micrometer 21, through which has been inserted collimator housing 1. Target 5 would appear to the patient in the space generally indicated by the numeral 24.

It should be understood that the apparatus of the present invention may be constructed of a variety of materials, depending upon the anticipated manner of use of the device. For surgical usages, the device should be in relevant pan made of stainless steel or other well-known surgical instrument compositions. The apparatus may be pre-packaged in a sterilized form to be opened during the procedure. The apparatus may also be manufactured as a one-use disposable instrument, or as a reusable piece of equipment which merely needs to be auto-claved prior to its reuse.

A disposable type of instrument could be manufactured at much less expense by utilizing plastic components. A device of this type, while usable in surgical routines if sterilized, would also be available for non-professional consumer use at home, should such be desired. If this were the case, the user would merely support the apparatus by hand the appropriate distance from the eye, bringing into focus the resolution target, with the refractive shift of the eye then indicated by the indicia located on sleeve 10. A device of this type could also be used at schools and in other situations where a low cost apparatus would be advantageous.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of measuring the visual acuity of the human eye during and immediately after ocular surgery, said surgery being of the type wherein a fixation ring is positioned upon the cornea so as to be coaxial with the visual axis of the eye and a support housing is coaxially supported upon said fixation ring, said support housing having a cylindrical bore extending coaxially above the visual axis of the eye, which comprises:

(a) inserting a measuring means into said cylindrical bore of said support housing, said measuring means having a smooth, cylindrical profile complementary to that of said cylindrical bore so as to be laterally stable when inserted therein and a flange for abutting an upper surface of said support housing so as to be stably seated upon said support housing after insertion, said measuring means thus being supported anterior to, and in line with the visual axis of, said eye; and (b) measuring the visual acuity of said eye using patient responses to visual prompts emanating from a target contained within said measuring means.

2. A method for measuring the visual acuity of a human eye according to claim 1, wherein said measuring means has an ocular aperture which is positioned approximately 6 mm from said eye upon insertion of said measuring means within said cylindrical bore of said support housing.

3. A method for measuring the visual acuity of a human eye according to claim 1, which further comprises placing a powerless conformal contact lens on said eye, should the epithelium of said eye have been removed, so as to provide an optically transmissive surface while not influencing the absolute refraction of said eye during measurement.

4. A method for measuring the visual acuity of a human eye according to claim 1, wherein said support housing is a micrometer housing and nut assembly.

5. A visual acuity collimator for measuring the visual acuity of the human eye during and immediately after ocular surgery, said surgery being of the type wherein a fixation ring is positioned upon the cornea so as to be coaxial with the visual axis of the eye and a support housing is coaxially supported upon said fixation ring, said support housing having a cylindrical bore extending coaxially above the visual axis of the eye, comprising:

(a) an elongate housing having a smooth, cylindrical profile complementary to that of said cylindrical bore so as to be laterally stable upon insertion therein and a flange for abutting an upper surface of said support housing so as to be stably seated upon said support housing after insertion, said housing further having an ocular aperture;

(b) a collimating lens positioned within said housing adjacent to said aperture;

(c) a resolution target positioned within said housing above said collimating lens;

(d) means for illuminating said resolution target;

(e) means for adjusting the degree of separation between said collimating lens and said resolution target; and (f) indicia means for indicating measured visual acuity, said indicia means being positioned above said flange of said housing.

6. A visual acuity collimator according to claim 5, wherein said means for illuminating comprises a manually actuated, battery powered incandescent bulb, said bulb being located above said resolution target.

7. A visual acuity collimator according to claim 5, wherein said means for adjusting the degree of separation between said collimating lens and said resolution target comprises a piston threadably connected to the interior of said housing above said collimating lens, said piston supporting said resolution target such that turning said piston adjusts the degree of separation between said lens and said target.

8. A visual acuity collimator for use in measuring the acuity of a human eye during and immediately after ocular surgery, which collimator may be supported for use by well known ocular surgical instruments, comprising:

(a) a smooth, cylindrical elongate housing having an ocular aperture at one end and a flange at the other end, said housing being insertable into, and stably received in, a cylindrical bore of a micrometer casing or other ocular platform such that said flange supports said housing within said casing or platform in a position whereby said ocular aperture is approximately 6 mm from said eye;

(b) a collimating lens positioned within said housing adjacent to said aperture;

(c) a piston threadably connected to the interior of said housing above said collimating lens, said piston supporting a resolution target above said lens and having a neck that extends through said flange and connects to a knob, such that turning said knob adjusts the degree of separation between said lens and said target, said neck having thereon indicia for indicating measured visual acuity; and (d) a manually actuated, battery powered light source, said light source being housed within said housing above said resolution target.

9. A visual acuity collimator according to claim 8 wherein said batteries for said light source are located within said knob and wherein said light source is actuated by the manual rotation of a cap that is threadably connected to said knob.

* * * * *